(12) United States Patent
Sano

(10) Patent No.: US 6,979,427 B2
(45) Date of Patent: Dec. 27, 2005

(54) APPARATUS FOR PREPARING SOLUTION

(75) Inventor: Yoshihiko Sano, Osaka (JP)

(73) Assignee: Nipro Corporation, Osaka (JP)

(*) Notice: Subject to any disclaimer, the term of this patent is extended or adjusted under 35 U.S.C. 154(b) by 771 days.

(21) Appl. No.: 09/879,966

(22) Filed: Jun. 14, 2001

(65) Prior Publication Data

US 2001/0052488 A1   Dec. 20, 2001

(30) Foreign Application Priority Data

Jun. 15, 2000  (JP) .............................. 2000-179347

(51) Int. Cl.⁷ ............................................ B01D 61/26
(52) U.S. Cl. ................. 422/261; 210/321.71; 210/97; 210/647
(58) Field of Search .................. 422/255, 261; 210/321.71, 97, 647

(56) References Cited

U.S. PATENT DOCUMENTS

| | | | |
|---|---|---|---|
| 4,096,059 A | | 6/1978 | Pinkerton .................. 210/22 A |
| 4,935,125 A | * | 6/1990 | Era et al. ..................... 210/101 |
| 6,274,034 B1 | * | 8/2001 | Nikaido et al. ................ 210/97 |
| 6,649,057 B2 | * | 11/2003 | Sano ..................... 210/321.71 |
| 6,656,355 B2 | * | 12/2003 | Sano ..................... 210/321.71 |
| 6,749,818 B2 | * | 6/2004 | Sano et al. .................. 422/255 |

FOREIGN PATENT DOCUMENTS

| DE | 32 34 119 C1 | 11/1983 |
|---|---|---|
| JP | 7-303694 A | 11/1995 |

* cited by examiner

*Primary Examiner*—E. Leigh McKane
(74) *Attorney, Agent, or Firm*—Kubovcik & Kubovcik

(57) ABSTRACT

A cost effective apparatus for preparing solutions is provided. The apparatus includes a chamber which is divided by a movable partition into two compartments, a dissolving solution supply line for supplying dissolving solution to a first compartment of the chamber, a solution tank, a solution preparing line connecting the solution tank and the first compartment of the chamber, a solution preparing line connecting the solution tank and a second compartment of the chamber, and a transporting pump provided between the solution tank and the second compartment, and a solution transporting line for transporting the solution prepared in the solution tank and that has been transported to the second compartment to the point of use. The transporting pump may alternatively be provided between the first compartment and the solution tank.

8 Claims, 2 Drawing Sheets

Figure 1:
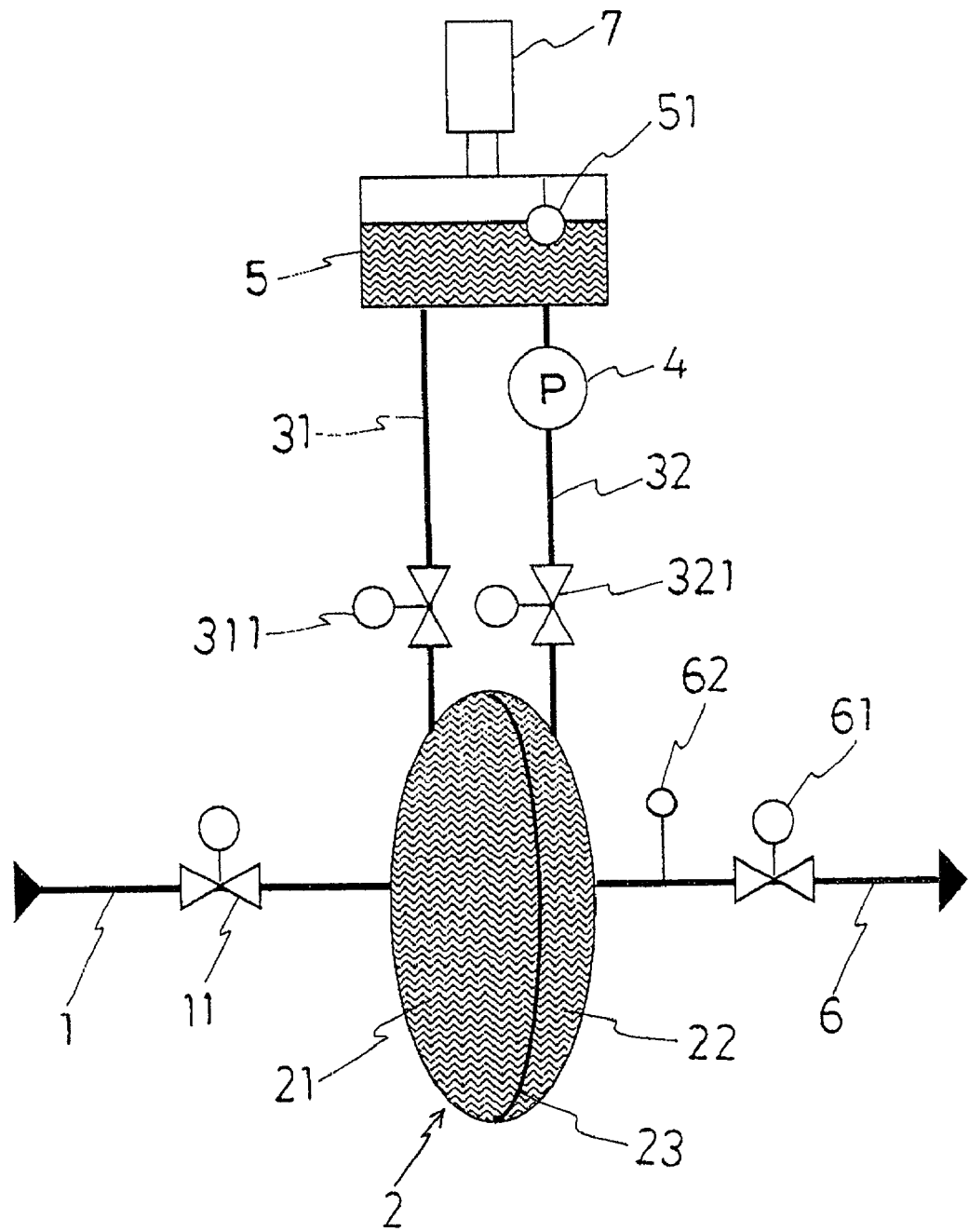

APPARATUS FOR PREPARING SOLUTION

TECHNICAL FIELD OF THE INVENTION

The present invention relates to an apparatus for preparing solutions by dissolving powder (including granulated powder) in a dissolving solution. The apparatus for preparing solutions in the present invention is especially suitable for preparing dialysate.

BACKGROUND OF THE INVENTION

Hitherto, preparation of solutions has been carried out in a tank system. In the tank system, prescribed quantities of dissolving solution (solvent) and powder are introduced into a solution tank and stirred by a stirring pump or a stirring blade and mixed to form a solution. The prepared solution is transferred to a point of use by a delivery pump. At this time, the level of the surface of the solution in the solution tank is lowered, and a negative pressure is generated in the solution tank and thus outside air is introduced into the solution tank. The introduction of air occurs in the tank system because the solution tank is generally opened to the air to prevent breakage of the solution tank itself by a negative pressure generated therein. Therefore, in many cases, an air filter is provided at a portion opened to the air to prevent bacteria or the like contained in the outside air from entering. The use of an air filter results in problems and a high cost for replacing the air filter on a regular basis. As a matter of fact, there are cases where a filter that prevents only dust is used, or even no filter is used considering the problems and cost. In addition, in a tank system, when an attempt is made to prepare a large quantity of solution at a time, a large solution tank is necessary, thereby disadvantageously increasing the size of the apparatus itself. Moreover, since many stirring pumps and delivery pumps are necessary, the operating noise may disadvantageously be too loud.

With a view to the circumstances described above, an object of the present invention is to provide a cost effective apparatus for preparing solutions in which replacement of an air filter for preventing bacteria or the like from entering into the solution tank is essentially unnecessary, and miniaturization of the entire system and lowering of operation noise are possible.

SUMMARY OF THE INVENTION

After dedicated studies, the inventor found that the above-described object can be achieved by utilizing a chamber which is divided by a movable partition into two compartments so that the solution can be prepared within a circuit containing these two compartments while substantially preventing outside air from entering therein, and reached the present invention. Stated differently, the present invention is an apparatus for preparing solutions comprising: a chamber which is divided by a movable partition into two compartments, a dissolving solution supply line for supplying a dissolving solution to the first compartment of the chamber, a solution preparing line connecting the first compartment and the second compartment of the chamber, a solution tank and a transporting pump provided in the solution preparing line, and a solution transporting line for transporting solution prepared in the solution tank and transported to the second chamber to the point of use.

The solution tank may be provided on its upper portion with a powder supply means and with a liquid level detecting sensor therein. The dissolving solution supply line may be provided with a second dissolving solution supply line. The apparatus for preparing solutions of the present invention is preferably constructed in such a manner that the dissolving solution supply line, the solution preparing line, and the solution transporting line are further connected with a second chamber which is divided by a movable partition into two compartments so that the preparation of solutions can be performed consecutively and continuously.

BRIEF DESCRIPTION OF THE DRAWINGS

FIG. 1 is a schematic system diagram showing an embodiment of the present invention.

FIG. 2 is a schematic system diagram showing another embodiment of the present invention.

DETAILED DESCRIPTION OF THE INVENTION

Referring now to the drawings, embodiments of the present invention will now be described.

FIG. 1 is a circuit diagram showing an embodiment of the present invention, and FIG. 2 is a circuit diagram showing another embodiment of the present invention.

The apparatus for preparing solutions in the present invention comprises, as shown in FIG. 1, a chamber 2 the inside of which is divided by a movable partition 23 such as a flexible diaphragm into two compartments 21, 22; a dissolving solution supply line 1 for supplying dissolving solution to the first compartment 21 of the chamber 2; a solution tank 5; a solution preparing line 31 connecting the solution tank 5 and the first compartment 21 of the chamber 2, a solution preparing line 32 connecting the solution tank 5 and the second compartment 22 of the chamber 2; a transporting pump 4 provided between the solution tank 5 and the second compartment 22; and a solution transporting line 6 for transporting a solution prepared in the solution tank 5 and transported to the second compartment 22 to the point of use. The transporting pump 4 may alternatively be provided between the first compartment 21 and the solution tank 5. In such a case, the action is slightly different.

The dissolving solution supply line 1, the solution preparing lines 31, 32, and the solution transporting line 6 are provided with switch valves 11, 311, 321, and 61, respectively. The solution tank 5 is preferably provided with a liquid level detecting sensor 51 therein, and with a powder supply means 7 on the upper portion thereof. The powder supply means 7 may be provided with an air filter (not shown) for preventing contamination caused by incoming outside air. For the operation of solution preparation, the switch valves 11, 311, and 61 are first opened and a dissolving solution is supplied from a dissolving solution supply source (not shown) to the first compartment 21 of the chamber 2 via the dissolving solution supply line 1. Then, air contained in the second compartment 22 is discharged through the solution transporting line 6, and thus the movable partition 23 moves toward the second compartment 22. The movement of the movable partition 23 continues until the capacity of the second compartment 22 becomes zero. In other words, movement of the partition 23 continues until a quantity of dissolving solution equal to the capacity of the chamber 2 fills the first compartment 21. The supply of the dissolving solution is continued and the dissolving solution is then supplied to the solution tank 5 through the solution preparing line 31. When the level of the dissolving solution supplied to the solution tank 5 reaches a prescribed level (that can be determined arbitrarily), the liquid level detecting sensor 51 is actuated to close the switch valves 11 and 61, and the switch valve 321 is opened and the transporting pump 4 is operated. The supply of powder to the solution tank 5 is continuously performed from the beginning to the end of the operation of the transporting pump 4, for example.

When the transporting pump 4 is operated, the solution in the solution tank 5 (a mixed liquid of powder and dissolving solution) is supplied to the second compartment 22 through the solution preparing line 32, and simultaneously, dissolving solution in the first compartment 21 of the same quantity as the quantity of solution supplied to the second compartment 22 is supplied to the solution tank 5 through the solution preparing line 31. At this time, the movable partition 23 is caused to move toward the first compartment 21. The movement of the movable partition 23 continues until the capacity of the first compartment 21 becomes zero, i.e., until a quantity of the solution equal to the capacity of the chamber 2 fills the second compartment 22. During this solution preparing process, the liquid level in the solution tank 5 is maintained at a constant level, and thus an influx of outside air into the solution tank 5 hardly occurs.

The solution transporting line 6 between the second compartment 22 and the switch valve 61 is provided with a pressure gauge 62. When this pressure gauge 62 detects an increase of internal pressure of the second compartment 22 (when the capacity of the first compartment 21 becomes zero, the internal pressure of the second compartment 22 increases), the transporting pump stops, the switch valves 311 and 321 are closed, and the switch valves 11 and 61 are opened to again supply the dissolving solution to the first compartment 21 of the chamber 2 from the dissolving solution supply source through the dissolved liquid supply line 1. At this time, the movable partition 23 moves toward the second compartment 22, and the solution in the second compartment 22 is transported through the solution transporting line 6 to the point of use. The movement of the movable partition 23 and the transportation of the solution in the second compartment 22 to the point of use continue until the capacity of the second compartment 22 becomes zero, in other words, until a quantity of dissolving solution equal to the capacity of the chamber 2 fills the first compartment 21. When the capacity of the second compartment 22 becomes zero, the internal pressure of the solution transporting line 6 suddenly drops. When the drop of the internal pressure in the solution transporting line 6 is detected by a pressure gauge 62, the switch valves 311 and 321 are opened, the switch valves 11 and 61 are closed and the transporting pump 4 is operated, and thus the dissolving solution is supplied through the solution preparing line 31 to the solution tank 5 and mixed with powder continuously supplied to the solution tank 5, and supplied to the second compartment 22 through the solution preparing line 32. The same procedures are repeated to prepare the solution.

Figure 2:
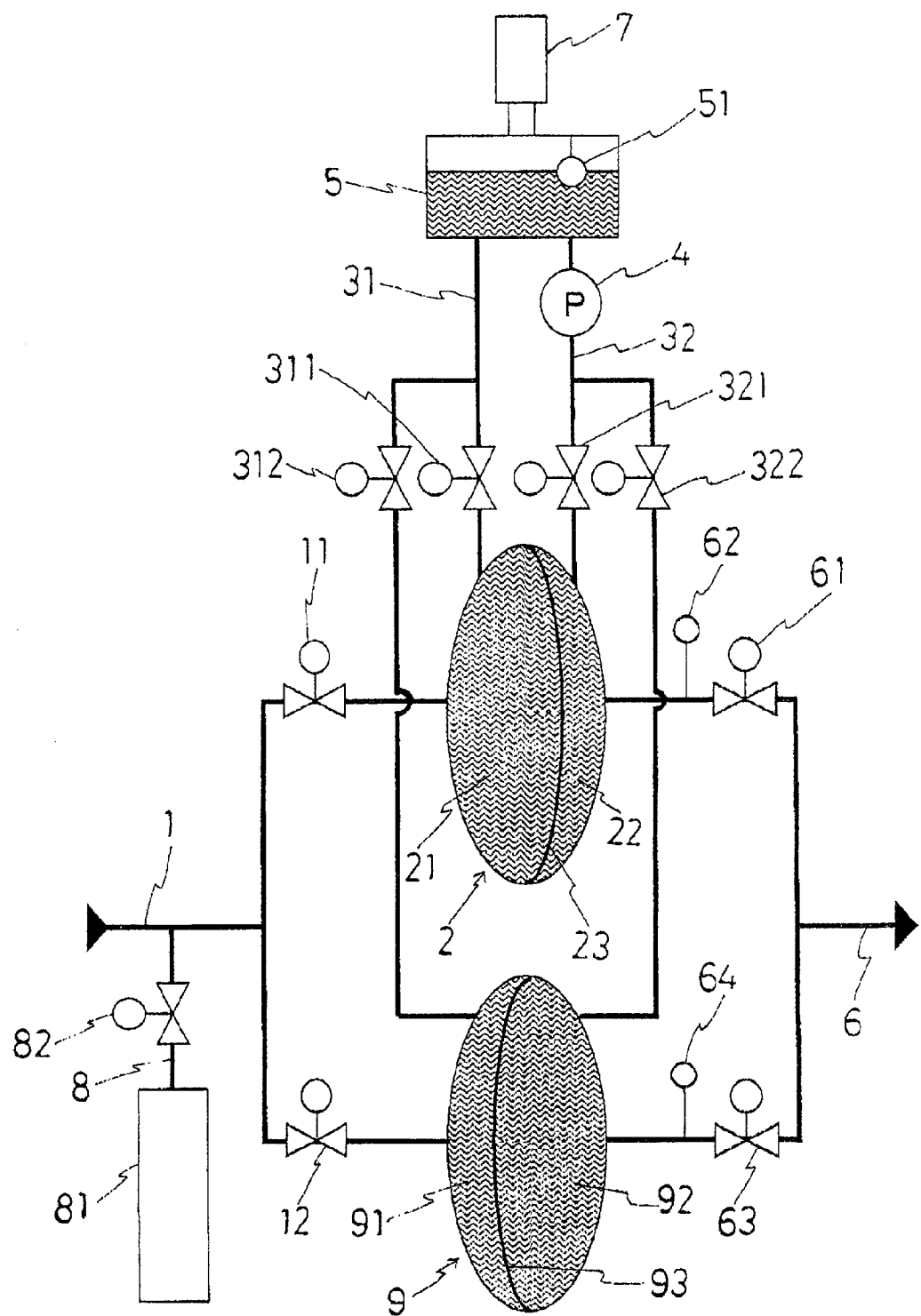

The apparatus for preparing solution in the present invention may be constructed in such a manner that the dissolving solution supply line 1 is provided with a second dissolving solution supply line 8, as shown in FIG. 2. The second dissolving solution supply line 8 generally comprises a second dissolving solution supply source 81 and a switch valve 82. The apparatus for preparing solution in the present invention may be constructed in such a manner that a second chamber 9, the inside of which is divided by a movable partition 93 into two compartments, is connected to the dissolving solution supply line 1, the solution preparing lines 31, 32, and the solution transporting line 6 as shown in FIG. 2, so that the preparation of solution can be performed continuously. In the figure, the reference numerals 12, 312, 322 and 63 designate switch valves and 64 designates a pressure gauge.

In the case of the apparatus for preparing solutions shown in FIG. 2, preparation of a solution is continuously performed between the chamber 2 and the second chamber 9. First, supply of the dissolving solution to the chamber 2 is performed as in the case of the apparatus for preparing solutions shown in FIG. 1 with the switch valve 321 connected to the chamber 2 and the switch valves 12, 312, 322, and 63 connected to the second chamber 9 closed. Then the switch valves 11 and 61 are closed and the switch valve 321 is opened and the transporting pump 4 caused to operate to prepare the solution. The supply of the dissolving solution to the first compartment 91 of the second chamber 9 is performed by opening the switch valves 12 and 63 while the switch valves 11 and 61 are closed and the transporting pump 4 is in operation. When a drop of the internal pressure in the solution transporting line 6 is detected by the pressure gauge 64, the supply of the dissolving solution to the first compartment 91 of the second chamber 9 terminates and the switch valves 12 and 63 are closed. When preparation of the solution on the chamber 2 side terminates, the transporting pump 4 stops, the switch valves 311 and 321 are closed, and the switch valves 11 and 61 are opened to supply the dissolving solution to the first compartment 21, and simultaneously, the solution is transported to the point of use. When a drop of the internal pressure of the solution transporting line 6 is detected by the pressure gauge 62, the supply of the dissolving solution to the first compartment 21 and transportation of the solution to the point of use terminate, and the switch valves 11 and 61 are closed. Simultaneously, the switch valves 312 and 322 connected to the second chamber 9 are opened and the transporting pump 4 is operated to perform the preparation of the solution on the second chamber 9 side. When the preparation of solution on the second chamber 9 side terminates, the transporting pump 4 is stopped, the switch valves 312 and 322 are closed, and the switch valves 12 and 63 are opened to perform the supply of the dissolving solution to the first compartment 91, and simultaneously the solution is transported to the point of use. When a drop of the internal pressure of the solution transporting line 6 is detected by the pressure gauge 64, the supply of the dissolving solution to the first compartment 91 and the transportation of the solution to the point of use terminate, and the switch valves 12 and 63 are closed. Simultaneously, the switch valves 311 and 321 connected to the chamber 2 are opened and the transporting pump 4 is operated to perform the preparation of the solution on the chamber 2 side. In the same manner, the supply of the dissolving solution on the chamber 2 side and the second chamber preparation of the solution and the transportation thereof to the point of use are alternatively repeated. The supply of the second dissolving solution can be performed by opening the switch valve 82 as appropriate.

As is clear from the description above, the equipment for transporting liquid of the present invention is advantageous in terms of cost because an air filter and a stirring pump are not necessary, and the number of the delivery pumps can be reduced. Since a large solution tank is not necessary, miniaturization of the system itself is possible. Since there is only one delivery pump used, the operating noise can significantly be reduced.

What is claimed is:

1. An apparatus for preparing solution comprising:
   a chamber which is divided by a movable partition into first and second compartments;

a first dissolving solution supply line connected to the first compartment of said chamber for supplying a dissolving solution to the first compartment;

a solution preparing line connecting the first compartment and the second compartment of said chamber;

a solution tank and transporting pump provided in said solution preparing line;

a powder supply means provided on the solution tank for supplying powder to said solution tank; and a solution transporting line connected to the second compartment of said chamber for transporting a solution that is prepared in said solution tank and that has been transported to the second chamber from said second chamber to the point of use.

2. An apparatus for preparing solution claimed in claim 1, further comprising a liquid level detecting sensor provided in the solution tank.

3. An apparatus for preparing solution claimed in claim 2, wherein the first dissolving solution supply line is provided with a second dissolving solution supply line.

4. An apparatus for preparing solution claimed in claim 3, further comprising a second chamber which is divided by a movable partition into two compartments, said second chamber being connected to the dissolving solution supply line, the solution preparing line, and the solution transporting line to enable the consecutive preparation of solution.

5. An apparatus for preparing solution claimed in claim 2, further comprising a second chamber which is divided by a movable partition into two compartments, said second chamber being connected to the dissolving solution supply line, the solution preparing line, and the solution transporting line to enable the consecutive preparation of solution.

6. An apparatus for preparing solution claimed in claim 1, wherein the first dissolving solution supply line is provided with a second dissolving solution supply line.

7. An apparatus for preparing solution claimed in claim 6, further comprising a second chamber which is divided by a movable partition into two compartments, said second chamber being connected to the dissolving solution supply line, the solution preparing line, and the solution transporting line to enable the consecutive preparation of solution.

8. An apparatus for preparing solution claimed in claim 1, further comprising a second chamber which is divided by a movable partition into two compartments, said second chamber being connected to the dissolving solution supply line, the solution preparing line, and the solution transporting line to enable the consecutive preparation of solution.

* * * * *